US008992077B2

(12) United States Patent
Simmonds (10) Patent No.: US 8,992,077 B2
(45) Date of Patent: Mar. 31, 2015

(54) ULTRASENSITIVE RATIOMETRIC CAPACITANCE DILATOMETER AND RELATED METHODS

(71) Applicant: Quantum Design International, Inc., San Diego, CA (US)

(72) Inventor: Michael Bancroft Simmonds, Bozeman, MT (US)

(73) Assignee: Quantum Design International, Inc., San Diego, CA (US)

(*) Notice: Subject to any disclaimer, the term of this patent is extended or adjusted under 35 U.S.C. 154(b) by 0 days.

(21) Appl. No.: 14/042,665

(22) Filed: Sep. 30, 2013

(65) Prior Publication Data

US 2014/0254624 A1 Sep. 11, 2014

Related U.S. Application Data (60) Provisional application No. 61/774,256, filed on Mar. 7, 2013.

(51) Int. Cl.
G01N 25/56 (2006.01)
G01N 25/16 (2006.01)
G01N 27/22 (2006.01)

(52) U.S. Cl.
CPC ............ G01N 25/16 (2013.01); G01N 27/226 (2013.01)
USPC .......................................................... 374/56

(58) Field of Classification Search
USPC ..................................................... 374/55, 56
See application file for complete search history.

(56) References Cited

U.S. PATENT DOCUMENTS

| 3,525,251 A | | 8/1970 | Adrian Marcu et al. |
| 3,729,991 A | * | 5/1973 | Hardway, Jr. ............. 73/862.337 |
| 4,453,398 A | * | 6/1984 | Demirel et al. ................... 73/38 |
| 6,718,281 B2 | | 4/2004 | Duncan et al. |

(Continued)

FOREIGN PATENT DOCUMENTS

| SU | 219260 | 5/1968 |
| SU | 1661634 | 7/1991 |

OTHER PUBLICATIONS

J. J. Neumeier, R. K. Bollinger, G. E. Timmins, C. R. Lane, R. D. Krogstad, and J. Macaluso, "Capacitive-based dilatometer cell constructed of fused quartz for measuring the thermal expansion of solids", Review of Scientific Instruments, vol. 79, 033903, 2008.*

(Continued)

*Primary Examiner* — Lisa Caputo
*Assistant Examiner* — Nasir U Ahmed (57) ABSTRACT

An ultrasensitive ratiometric capacitance dilatometer and related methods are described. The dilatometer provides a capacitance measurement based on a ratiometric capacitance, or the capacitance ratio measured between two or more parallel plate capacitors of the dilatometer. In this regard, an absolute capacity bridge is not required, and even more advantageously, the effects of adsorbed gas are greatly reduced compared to conventional dilatometers. The ratiometric capacitance dilatometer provides a symmetrical configuration, which reduces the effects of temperature gradients. Moreover, certain embodiments provide a "v-groove design", wherein a first parallel plate capacitor forms an angle with a second parallel plate capacitor of the dilatometer along a key centerline of the dilatometer cell, which improves manufacturability due to simpler grinding, metalizing and assembly.

22 Claims, 8 Drawing Sheets

(56) References Cited

U.S. PATENT DOCUMENTS

| | | | |
|---|---|---|---|
| 7,526,961 B2 * | 5/2009 | Downie et al. | 73/718 |
| 7,766,547 B2 * | 8/2010 | Weppenaar et al. | 374/208 |
| 2013/0041244 A1 * | 2/2013 | Woias et al. | 600/381 |

OTHER PUBLICATIONS

PCT Search Report and Written Opinion for PCT/US2014/021940, issued Aug. 7, 2014, 6 Pages.

Neumeier J. J. et al. Capacitive-based dilatometer cell constructed of fused quartz for measuring the thermal expansion of solids. Review of Scientific Instruments 79, 033903 (2008).

Satoshi Abe et al., "A compact capacitive dilatometer for thermal expansion and magnetostriction measurements at millikelvin temperatures", Cryogenics, Mar. 16, 2012, 5 Pages, 52 (2012) 452-456.

* cited by examiner

ULTRASENSITIVE RATIOMETRIC CAPACITANCE DILATOMETER AND RELATED METHODS

CROSS-REFERENCE TO RELATED APPLICATIONS

This application claims benefit of priority with U.S. Provisional Ser. No. 61/774,256, filed Mar. 7, 2013, and titled "DILATOMETER"; the contents of which are hereby incorporated by reference.

BACKGROUND

1. Field of the Invention

This invention relates to high precision instruments known as dilatometers, which are designed to measure dimensional changes of a specimen brought about by changes in its environment; and more particularly, to such dilatometers configured for ratiometric measurement between two or more parallel plate capacitors, and related methods, such instruments being referred to herein as "ratiometric capacitance dilatometers".

2. Description of the Related Art

The coefficient of thermal expansion is a fundamental property of all materials; yet the capability of measuring thermal expansion is not readily available in most laboratories, especially at cryogenic temperatures on the order of few or a fraction of a degree Kelvin.

A dilatometer is an ultra-sensitive instrument for measuring dimensional changes of a material brought about by changes in its environment. Various applications for dilatometers may include: locating phase transitions in materials; predicting pressure effects in superconductors; characterizing cryogenic construction materials; magnetostriction studies or providing information that is complementary to heat capacity data.

A number of dilatometers have been proposed in the art, including: furnace and push rod dilatometers used in high temperature applications; resonant frequency dilatometers used in low temperature applications; piezo-resistive dilatometers which have been shown to provide modest resolution; and capacitive dilatometers which are the most sensitive of these instruments but also the most difficult to successfully implement. The embodiments herein will relate to improved capacitive dilatometers.

The capacitance dilatometer is designed to benefit from the ability to accurately measure changes in capacitance between two parallel plates. Because of this ability, such dilatometers are capable of measuring length changes on the order of a fraction of an Angstrom.

There is an interest in studying thermal expansion of various solids, and in particular, such solids under very low temperatures and/or within an applied magnetic field.

Thus, in addition to measuring thermal expansion of a material, it would be beneficial to collect data relating to dimensional changes of a given sample at very low temperatures and within various magnetic fields or gradients. Accordingly, various embodiments herein have been designed for use with the commonly owned and commercially available "Physical Property Measurement System" or "PPMS" of Quantum Design, Inc., which is a versatile, low temperature cryostat capable of providing an environment with temperatures between 0.05 K and 1000K, and with magnetic fields up to 16 T. The PPMS further provides automated, on-board temperature controlling and measuring ability. Although the PPMS is an exceptional platform for use with certain embodiments herein, it should be understood that other low temperature cryostats or similar systems may be similarly implemented and that the scope of the invention is not intended to be limited to practice with the above-described PPMS.

Recent advancements in the design and implementation of capacitive dilatometers are described in Schmiedeshoff et al., "Versatile and compact capacitive dilatometer", Review of Scientific Instruments 77, 123907 (2006). Schmiedeshoff describes a capacitive dilatometer having cylindrical geometry and fabricated from Copper. Copper is purportedly selected for its high thermal conductivity, machinability, relative insensitivity to high magnetic fields, and well known thermal expansion characteristics. However, although well known, copper alloys have high thermal expansions, and suffer from magnetic torque on induced eddy currents which result in a large contribution to the raw expansion data from the cell itself. This thermal expansion portion of the data must be subtracted in order to determine the expansion component attributed to the material sample. This correction is widely referred to as the "empty cell effect", whereas the correction takes into consideration an amount of noise attributed to thermal expansion of the empty cell.

Furthermore, miniature capacitance-based dilatometer expansion cells are almost universally constructed out of copper, copper beryllium or other copper alloys. This construction however suffers from the fact that insulating materials are needed to electrically isolate the capacitance plates from the body of the expansion cell which is also conducting. In practice, these copper alloy expansion cells will typically result in a large "empty cell effect" or background signal due to the large thermal expansion of the conductive materials and or the complex copper and insulating construction of the cell itself.

More recently, Neumeier et al. describe a dilatometer cell that can detect sub angstrom changes in length of solid specimens within the temperature range 5 K<T<350 K in "Capacitive-based dilatometer cell constructed of fused quartz for measuring the thermal expansion of solids", Review of Scientific Instruments 79, 033903 (2008). The Neumeier dilatometer is fabricated from an insulating fused silica (quartz), which provides low thermal expansion, and thus exhibits a smaller contribution of the cell's thermal expansion to the raw data for a reduced "empty cell effect".

Figure 1:
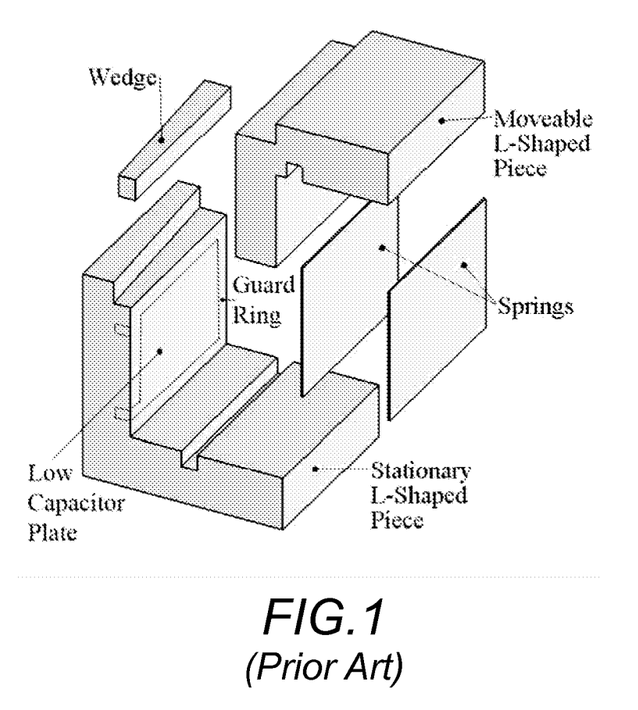
FIG. 1 shows a prior art dilatometer.

FIG. 1 illustrates the Neumeier cell having a stationary L-shaped base piece with a capacitor plate formed on an inner vertical surface, a moveable L-shaped piece having a second capacitor plate formed on a vertical surface configured to oppose the first capacitor plate, a wedge for wedging a sample between the L-shaped pieces, and a pair of springs for maintaining a counterpoise force against the direction of sample expansion. The cell body is composed of fused silica, or quartz.

Benefits of the Neumeier dilatometer cell include: low expansion due to the all fused-silica construction; the cell is not sensitive to magnetic field; the cell (per se) is not sensitive to temperature; the capacitance readout gives high resolution; large size gives a sizeable capacitance to measure; an Andeen-Hagerling bridge is an excellent off-the-shelf solution for capacitance readout; and the cell can accommodate a range of sample lengths.

Although an improvement over prior copper alloy type capacitive dilatometers, which themselves suffer from high thermal expansion, in practice, the Neumeier cell presents several problems when used within a low temperature cryostat, such as: capacity is affected by gas adsorption; an absolute capacitance measurement is required; and thermal gradients affect accuracy in $1^{st}$ order.

Moreover, in all of these capacitive prior art cells, the measurement is affected by gas adsorption and thermal gradients to first order; and measurement of the absolute capacitance is required which is difficult without very specialized and expensive instrumentation.

With the intense interest in expansion measurements of material solids, there continues a need for an improved capacitive dilatometer cell which addresses these and other practical needs in the art.

SUMMARY

An ultrasensitive ratiometric capacitance dilatometer and related methods are described. The dilatometer provides a capacitance measurement based on a ratiometric capacitance, or the capacitance ratio measured between two or more parallel plate capacitors of the dilatometer. In this regard, an absolute capacitance bridge is not required, and even more advantageously, the effects of adsorbed gas are greatly reduced compared to conventional dilatometers. The ratiometric capacitance dilatometer provides a symmetrical configuration, which reduces the effects of temperature gradients. Moreover, certain embodiments provide a "vgroove design", wherein a first parallel plate capacitor forms an angle with a second parallel plate capacitor of the dilatometer along a key centerline of the dilatometer cell, which improves manufacturability due to simpler grinding, metalizing and assembly. Other features and benefits will be illustrated and described in the following detailed description and the appended drawings.

DETAILED DESCRIPTION OF THE PREFERRED EMBODIMENTS

In the following description, for purposes of explanation and not limitation, details and descriptions are set forth in order to provide a thorough understanding of the invention. However, it will be apparent to those skilled in the art that the invention may be practiced in other embodiments that depart from these details and descriptions without departing from the spirit and scope of the invention. Certain embodiments will be described below with reference to the drawings, wherein illustrative features are denoted by reference numerals.

In the embodiments herein, a dilatometer cell is introduced which is configured to provide a ratiometric capacitance measurement for determining sample expansion. In the dilatometer cell, spacing between a series of metalized plates allows detection of changes in the length of the specimen. Unlike other dilatometers described in the prior art, the claimed embodiments utilize a ratiometric measurement technique which allows the cell to be first order insensitive to temperature gradients, exchange gas pressure and applied magnetic fields.

The cell is adapted for mounting in an isothermal chamber, and be rotated with respect to an applied magnetic field, thus making magnetostriction measurements possible in a wide range of temperature ranges.

DEFINITIONS

For purposes herein, a number of key terms are defined by the applicant as follows:

"centerline" is defined as an imaginary line or region of bisection between the first cell portion and the second cell portion of the ratiometric capacitance dilatometer cell, including angled protrusions and angled grooves, their surfaces and volumes;

"acute angle" is defined as an angle greater than 0° and less than 90°;

"obtuse angle" is defined as an angle greater than 90° and less than 180°; and

"counterpoise" is defined as a force or influence that balances or equally counteracts another.

EXAMPLES

Figure 2A:
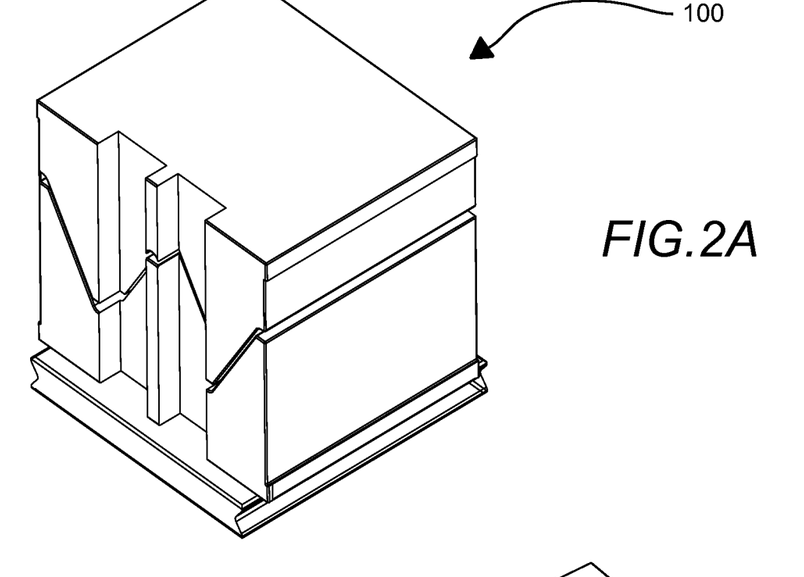
FIG. 2A shows a front perspective view of a ratiometric capacitance dilatometer cell in accordance with one embodiment; a front side, right side, and top side are shown.

Now turning to the drawings, FIG. 2A shows a front perspective view of a ratiometric capacitance dilatometer cell 100 in accordance with one embodiment; a front side, right side, and top side of the dilatometer cell are shown.

The dilatometer cell generally comprises a cube made up of a first cell portion having one or more angled protrusions and a second cell portion having one or more angled grooves, the first cell portion being configured to nest with the second cell portion such that one or more respective surfaces of the angled protrusions are configured to oppose and overlap with respective surfaces of the angled grooves. In this regard, the first and second cell portions are nested to form a volume of the dilatometer cell, with two or more overlapping surfaces (four overlapping surfaces are shown). The cell has a right side and a left side, each of the right and left sides are configured to about one of two planar sheets referred to herein as a "springs". A base portion is attached to the second cell portion, the base portion having opposing notches being disposed on opposite sides thereof. The opposing notches are adapted for mounting the dilatometer cell with a mounting assembly.

Figure 2B:
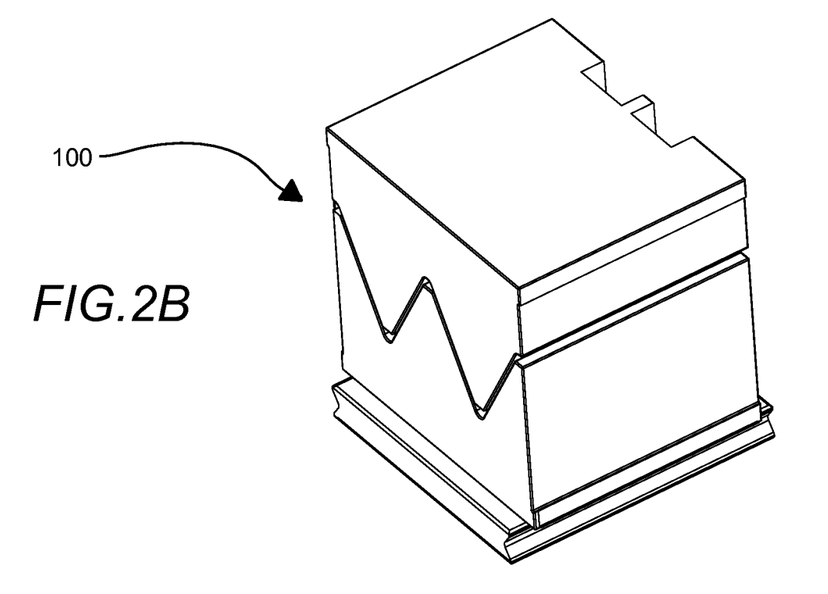
FIG. 2B shows a rear perspective view of the ratiometric capacitance dilatometer cell of FIG. 2A; a rear side, left side, and top side are shown.

FIG. 2B shows a rear perspective view of the ratiometric capacitance dilatometer cell 100 of FIG. 2A; a rear side, left side, and top side of the dilatometer cell are shown.

Although depicted as a cube in the illustrated embodiments, the dilatometer can alternatively comprise a cylindrical form or other geometric volume, however, symmetry in the dilatometer design is encouraged for purposes described herein. Those having skill in the art will appreciate that minor fabrication and design deviations will yield substantially similar results.

Additionally, although the cell is preferably fabricated from a fused silica (quartz), copper alloy and other materials can be used to make a similar dilatometer cell. For instance, fused silica might be preferable if operation in strong magnetic fields and temperature above 1 K are required, whereas a cell made of a conductive material, such as a copper alloy, might be preferable for use below 1 K and or in a vacuum environment.

Figure 3:
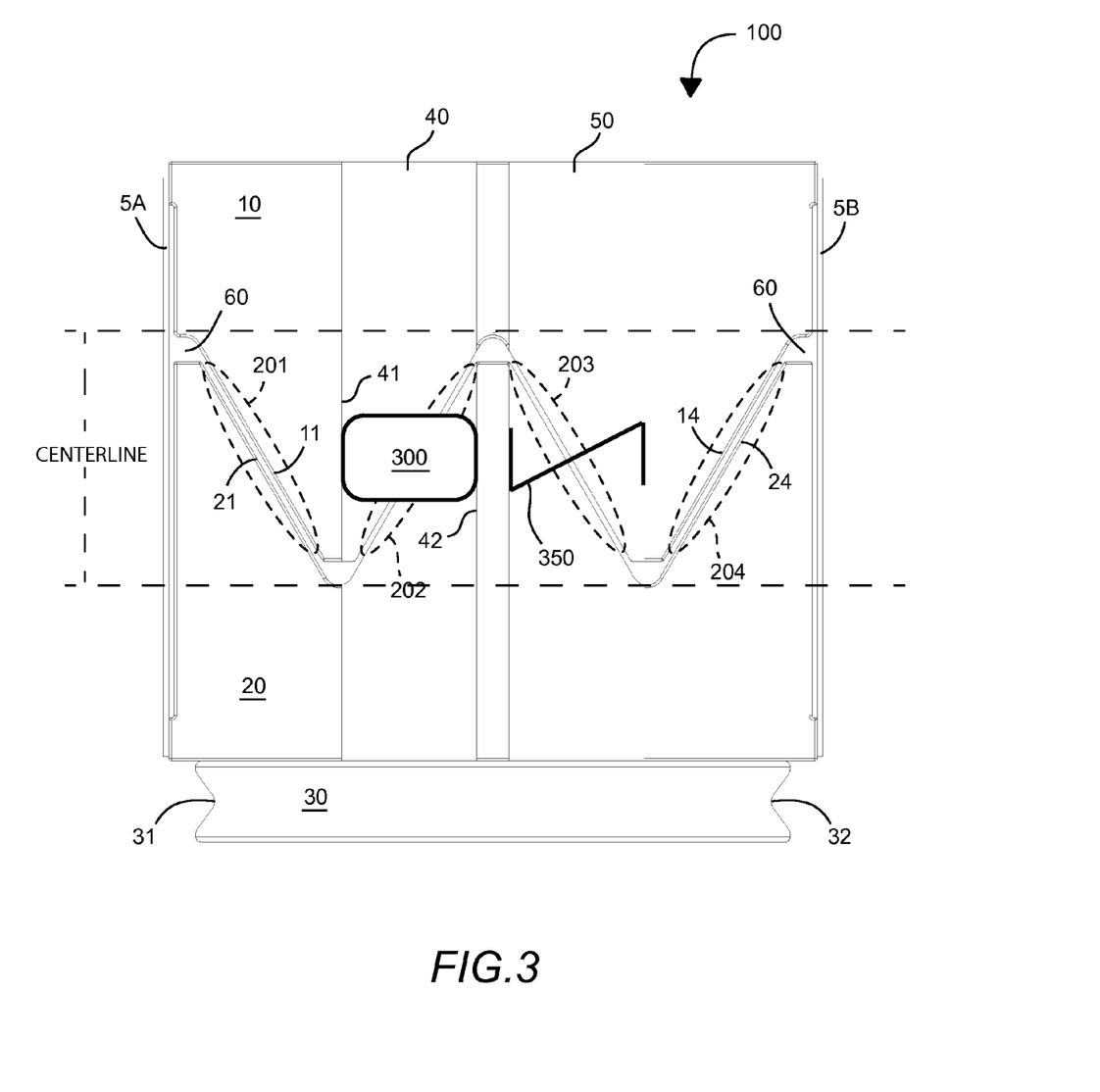
FIG. 3 shows a side view of the ratiometric capacitance dilatometer cell with a sample mounted within a first channel and a spring mounted within a second channel.

FIG. 3 shows a side view of the ratiometric capacitance dilatometer cell 100 with a sample 300 mounted within a first channel 40 and a spring 350 mounted within a second channel 50. The spring is optional, but preferred for providing a counterpoise force in a direction opposite of sample expansion.

Figure 4:
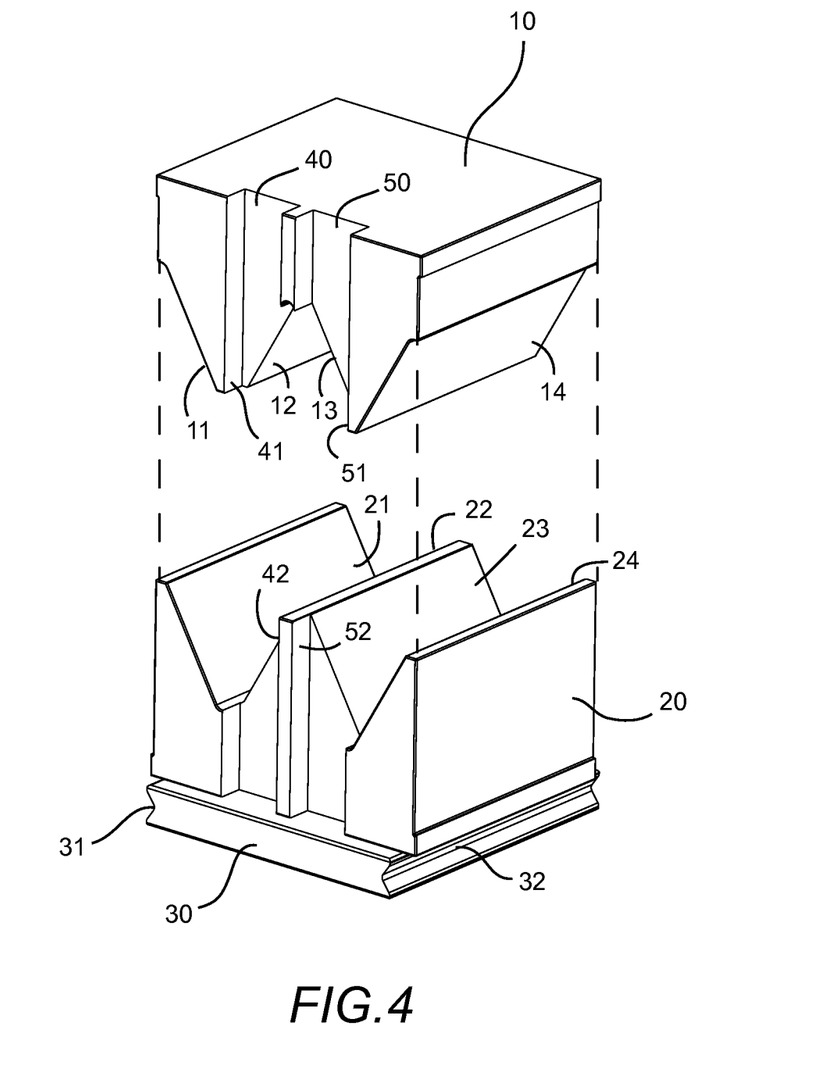
FIG. 4 shows an exploded view of the ratiometric capacitance dilatometer cell.

FIG. 4 shows an exploded view of the ratiometric capacitance dilatometer cell of FIG. 3.

As illustrated in FIGS. 3-4, the dilatometer cell comprises a first cell portion 10, a second cell portion 20, a base portion 30, a first spring 5a disposed on a left side of the dilatometer, and a second spring 5b disposed on a right side of the dilatometer.

The first cell portion 10 further comprises at least one angled protrusion (two are shown), each of the angled protrusions comprising a pair of planar surfaces oriented at an angle with respect to one another. Each of the planar surfaces are individually metalized or otherwise configured to form or couple with a conductive plate about an area of the respective planar surface. Thus, in the embodiment of FIGS. 3-4, the first cell portion comprises a first conductive plate 11 oriented at an angle with respect to a second conductive plate 12, and a third conductive plate 13 oriented at an angle with respect to a fourth conductive plate 14. Although four conductive plates are illustrated, the first cell portion can be configured with two or more conductive plates forming one or more angled protrusions. The left and right sides of the first cell portion can comprise an edge configured to receive and at least partially about a sheet spring 5A; 5B, respectively. The sheet spring can be glued or otherwise bonded to an exterior surface of each of the left and right sides of the first cell portion.

The bottom portion 20 further comprises at least one angled groove (two are shown), each of the angled grooves comprising a pair of planar surfaces oriented at an angle with respect to one another. Each of the planar surfaces are individually metalized or otherwise configured to form or couple with a conductive plate about an area of the respective planar surface. Thus, in the embodiment of FIGS. 3-4, the second cell portion comprises a first conductive plate 21 oriented at an angle with respect to a second conductive plate 22, and a third conductive plate 23 oriented at an angle with respect to a fourth conductive plate 24. Although four conductive plates are illustrated, the second cell portion can be configured with two or more conductive plates forming one or more angled grooves. The left and right sides of the second cell portion can comprise an edge configured to receive and at least partially abut a surface of the sheet spring 5A; 5B, respectively. The sheet spring can be glued or otherwise bonded to an exterior surface of each of the left and right sides of the second cell portion in a manner similar to that of the first cell portion.

When nested together, the first cell portion fits with the second cell portion with a small gap therebetween to create two or more parallel plate capacitors. The sheet springs 5A; 5B, respectively, may be configured to assist in maintaining a gap between the first and second cell portions. For instance, as illustrated in FIGS. 3-4, the first conductive plate 11 of the first cell portion 10 at least partially overlaps with the first conductive plate 21 of the second cell portion 20, forming a first parallel plate capacitor 201 having a first capacitive region defined by a gap extending between the first conductive plates 11; 21. Similarly, the second conductive plate 12 of the first cell portion 10 at least partially overlaps with the second conductive plate 22 of the second cell portion 20, forming a second parallel plate capacitor 202 having a second capacitive region defined by a gap extending between the second conductive plates 12; 22. Moreover, a third and a fourth parallel plate capacitor 203; 204, respectively, are illustrated as being disposed between the first and second cell portions. The third parallel plate capacitor is formed between conductive plate 13 and conductive plate 23; whereas the fourth parallel plate capacitor is formed between conductive plate 14 and conductive plate 24.

In the cell, the opposing conductive plates of the dilatometer cell form a capacitor having a capacitance C as a function of the surface area A, distance between the plates d, and the permittivity $\in$ of the medium existing between the plates:

$$C(T)=\in(T)[A(T)/d(T)];$$

for a given temperature T.

As the surfaces forming the respective conductive plates are paired and oriented with respect to one another at an angle, so are the respective parallel plate capacitors formed on these surfaces. Thus, the first parallel plate capacitor 201 is said to be oriented with the second parallel plate capacitor 202 at an angle therebetween. The angle between the first and second parallel plate capacitors can comprise one of: an obtuse angle, an acute angle or a right angle. In this regard, as a sample volume expands, one of the first and second parallel plate capacitors is configured to increase a gap therebetween and decrease capacitance as a function of the distance change, whereas another of the first and second parallel plate capacitors is configured to decrease a gap therebetween and increase capacitance as a function of the distance change. Therefore, the dilatometer is configured to provide a ratiometric measurement of the capacitance between the two or more capacitors, or the capacitance ratio, as opposed to direct capacitance readout. This ratiometric capacitance measurement, as described above, reduces the effects of adsorbed gas (the dilatometer is measured in a sample chamber of a cryostat containing cryogen gas), among other things.

In practice, electroplating may be preferred for forming the conductive plates; however, the conductive plates of the respective parallel plate capacitors can be formed from any method in the art for creating a metalized surface on a volume, such as attaching a conductive sheet, printing a conductive ink, or otherwise depositing metals or other conductive materials on a surface to be metalized.

Returning to the illustrated embodiment of FIGS. 3-4, a first channel 40 extends vertically across the gap 60 from the first cell portion to the second cell portion, and comprises a first wall 41 disposed on the first cell portion and a second wall 42 disposed on the second cell portion at a side opposite with respect to the first wall 41. In this regard, a sample 300 is inserted between the first wall 41 and the second wall 42 such that as the sample 300 increases in size, the first and second walls are configured to shift away from one another along the centerline of the cell. This shift results in a change in the capacitance which can be detected by an associated measurement system, such as for example a physical property measurement system (PPMS) manufactured by Quantum Design, Inc. as described above.

A second channel 50 may be optionally provided, the second channel 50 extends vertically across the gap 60 from the first cell portion to the second cell portion, and comprises a first wall 51 disposed on the first cell portion and a second wall 52 disposed on the second cell portion at a side opposite with respect to the first wall 51. The second channel is similar to the first channel as described above, however, instead of a sample the second channel is configured to receive a spring 350 for providing a counterpoise force in a direction opposite of sample expansion along the centerline of the cell.

A base 30 is provided for mounting the dilatometer 100 within a sample chamber of a specimen probe. In the illustrated embodiment, the base comprise a first notch 31 extending along a first side of the base and a second notch 32 extending along a second side of the base opposite of the first side. The base can be configured to receive a portion of a clip for maintaining the dilatometer cell against a mounting platform of a specimen probe or within a sample chamber thereof.

Figure 5:
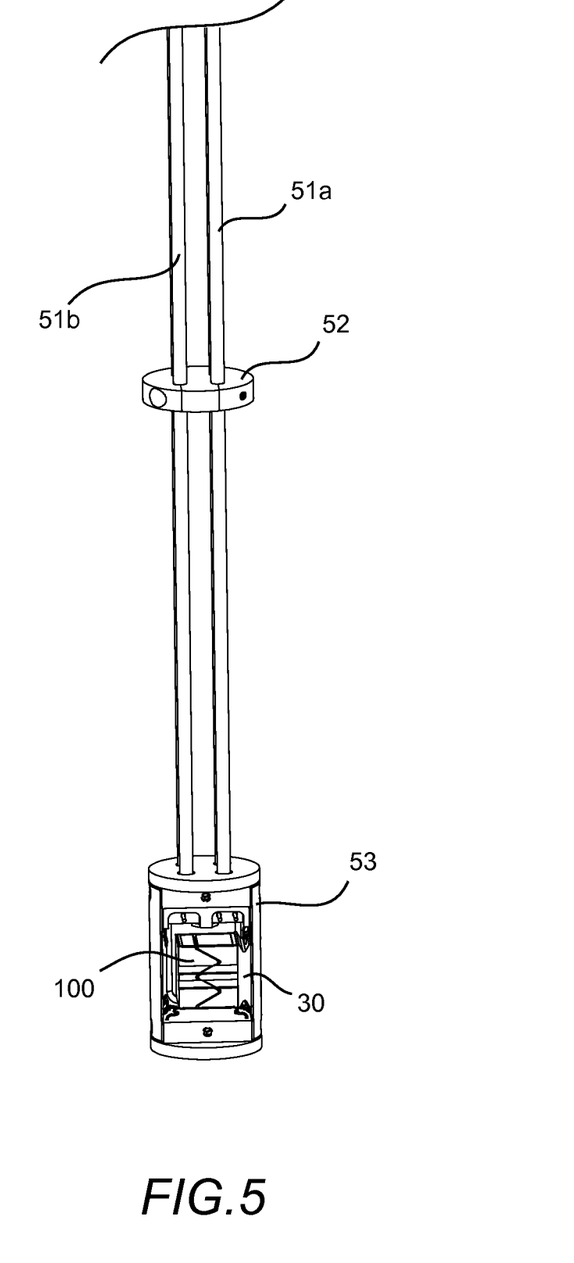
FIG. 5 shows a static specimen probe for mounting the ratiometric capacitance dilatometer cell in accordance with an embodiment.

FIG. 5 shows a static specimen probe containing the ratiometric capacitance dilatometer cell in accordance with an embodiment. The static probe comprises a probe shaft 51a; 51b extending from a proximal end to a distal end, and comprises a platform housing 53 disposed at the distal end. The probe may contain one or more radiation baffle spacers 52 for isolating the lower volume of the probe from radiation present in the upper portions. The platform housing comprises at least one fixed platform configured to receive a dilatometer cell mounted thereon. The dilatometer cell 100 is configured to be mounted at any angle with respect to an applied magnetic field, with said angle being fixed by the platform and associated mounting position of the attached dilatometer cell. For mounting, the dilatometer may comprise a base portion 30 designed to engage with a mounting platform of the probe.

Figure 6:
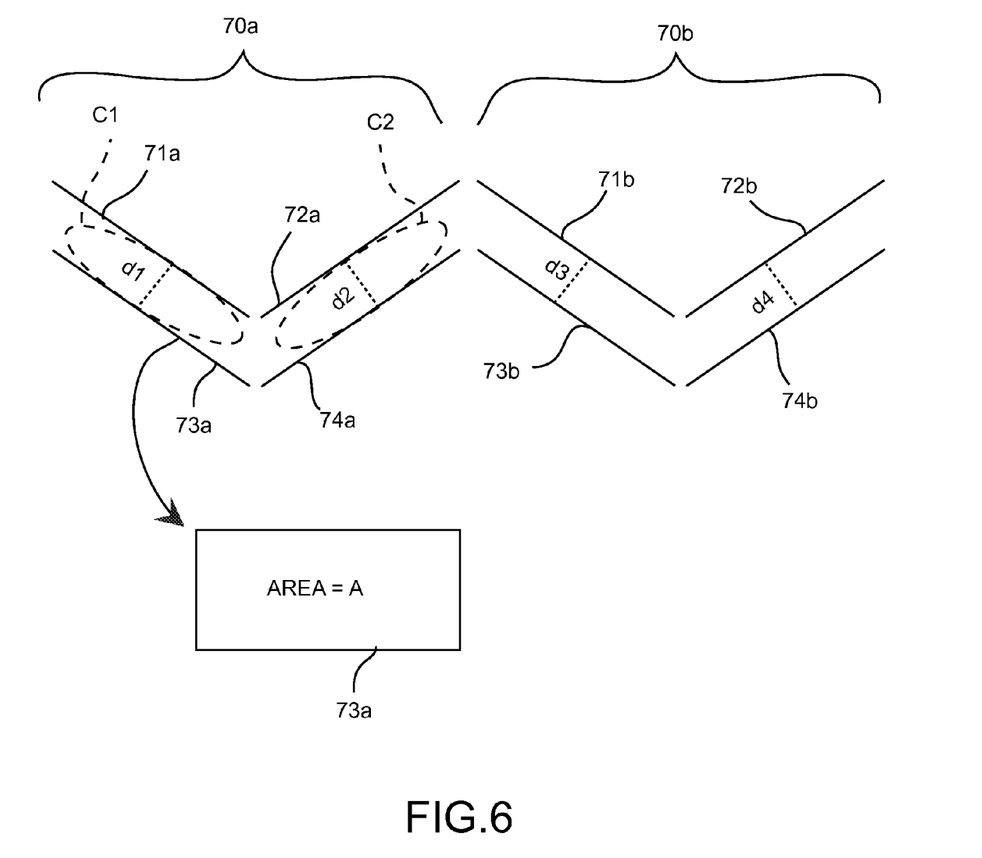
FIG. 6 shows an electrical configuration of the dilatometer cell.

FIG. 6 shows an electrical configuration of the dilatometer cell in accordance with an embodiment. Two sets of capacitors in a "parallel" configuration form the fixed (i.e. rigid with respect to the dilatometer cell probe in which it is mounted) transmitter positive plates, the fixed transmitter negative plates and the movable receiver plates which will be shifted either to the right or left according to the sample expansion or restriction. The shift of the receiver plates will reduce the gap and thus capacitance of the first set of capacitors, and increase the gap and thus capacitance of the second set of capacitors. Referring to FIG. 6, a first capacitor C1 is formed by a first transmitter negative plate 73a having an area "A" and being disposed in parallel with respect to a first receiver plate 71a at a distance d1 therefrom. A second capacitor C2 is formed by a first transmitter positive plate 74a having an associated area and being disposed in parallel with respect to a second receiver plate 72a. The first capacitor C1 and the second capacitor C2 form a first capacitor set 70a. The dilatometer may comprise two or more sets of capacitors as shown; wherein a third capacitor is formed by plates 71b and 73b at a distance d3 therebetween, and a fourth capacitor is formed by plates 72b and 74b at a distance d4 therebetween. The third and fourth capacitors form a second set of capacitors 70b.

In order to detect a change in expansion of a sample, a ratiometric measurement is performed between the two sets of capacitors with an effective area A and gaps d1 and d2. The capacitance of each capacitor is given by:

$$C1 = \in(T)A/d_1; \text{ and}$$

$$C2 = \in(T)A/d_2;$$

where:
$\in(T)$ is the dielectric constant of the gas between the capacitor plates;

At equilibrium $d_1 = d_2 = d$ is dictated by the length of the sample at room temperature and in a zero applied magnetic field.

When the sample expands by an infinitesimal amount x due to a change in temperature and/or applied magnetic field then the gaps in the capacitors will change to $d_1 = d+x$ and $d_2 = d-x$.

In order to keep the balance signal null (i.e. $V_{balance} = 0$) the microprocessor in the circuit will adjust the voltage amplitude ratio across the variable inductors by an amount $\Delta U$ to compensate for the change in gap across each of the two capacitors. The voltage across each capacitor will then be:

$$U_0 - \Delta U = I/(j\omega C_1); \text{ and}$$

$$U_0 + \Delta U = I/(j\omega C_2);$$

Eliminating I from these equations we have:

$$(U_0 - \Delta U)[\in A/(d+x)] = (U_0 + \Delta U)[\in A/(d-x)]$$

or solving for the sample expansion x we get:

$$x = -(\Delta U/U_0)d.$$

This result shows the important fact that the measurement of the sample expansion, is independent of the temperature dependent permittivity $\in(T)$ of the gas medium between the capacitor plates, thus greatly reducing the contribution of the gas adsorbed to capacitor's plates of the cell itself to the raw data of the dilatometer.

Figure 7:
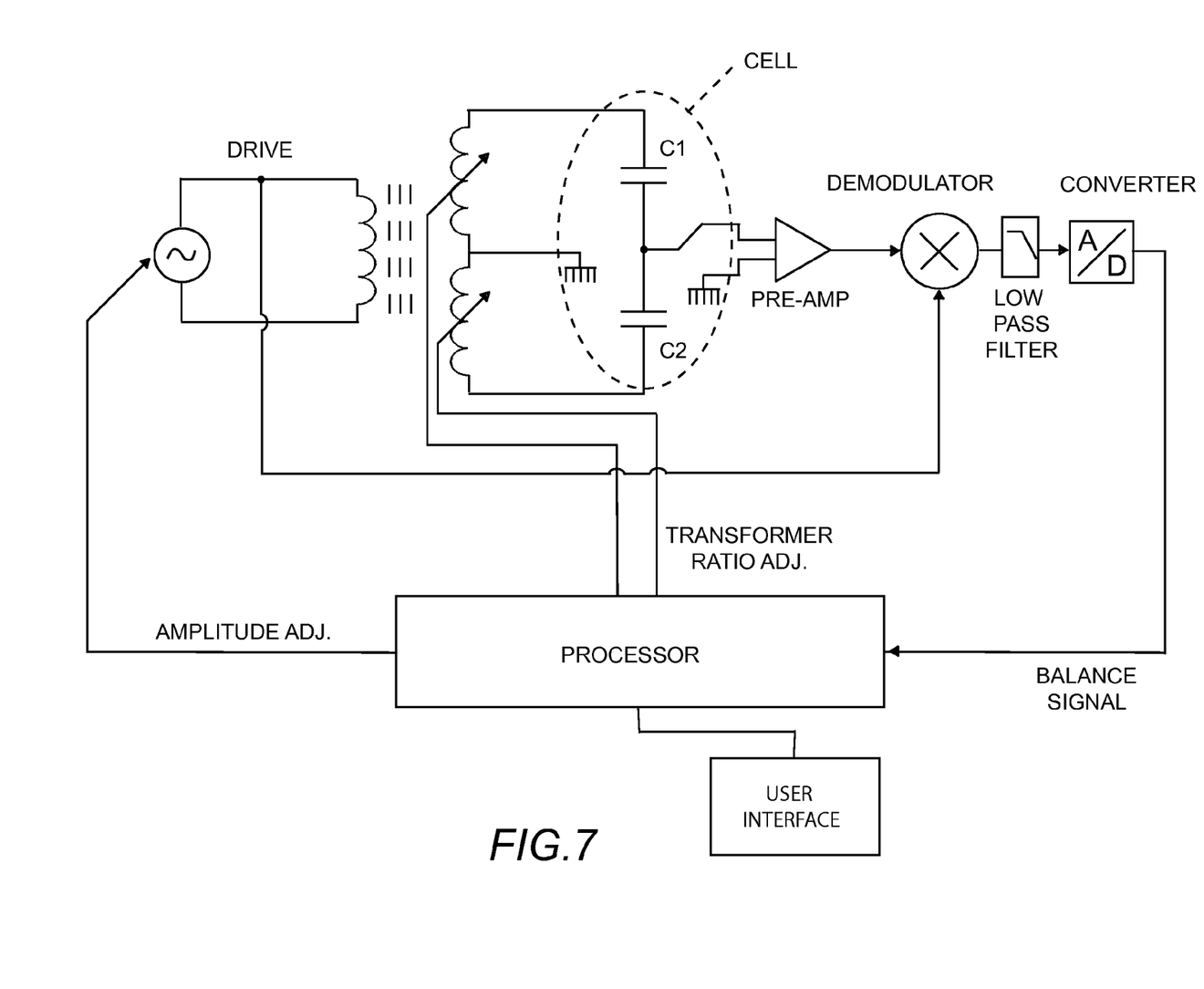
FIG. 7 shows an electrical schematic of the dilatometer cell and related detection system in accordance with an embodiment.

FIG. 7 shows an electrical schematic of the dilatometer cell and related detection system in accordance with an embodiment. A processor is coupled to a user interface and configured to measure a ratiometric change in capacitance of the dilatometer cell as a result of a corresponding dimensional change of a mounted sample. The processor is configured to receive a balance signal and adjust each of the amplitude of the drive signal and the ratio of the transformer signals. The dilatometer cell itself is indicated as the portion of the circuit contained within the dashed oval. The dilatometer cell comprises a first capacitor C1 and a second capacitor 2 as described above. The dilatometer cell is coupled to a pre-amp and an output signal is communicated through a demodulator, a low pass filter and an A/D converter.

Figure 8:
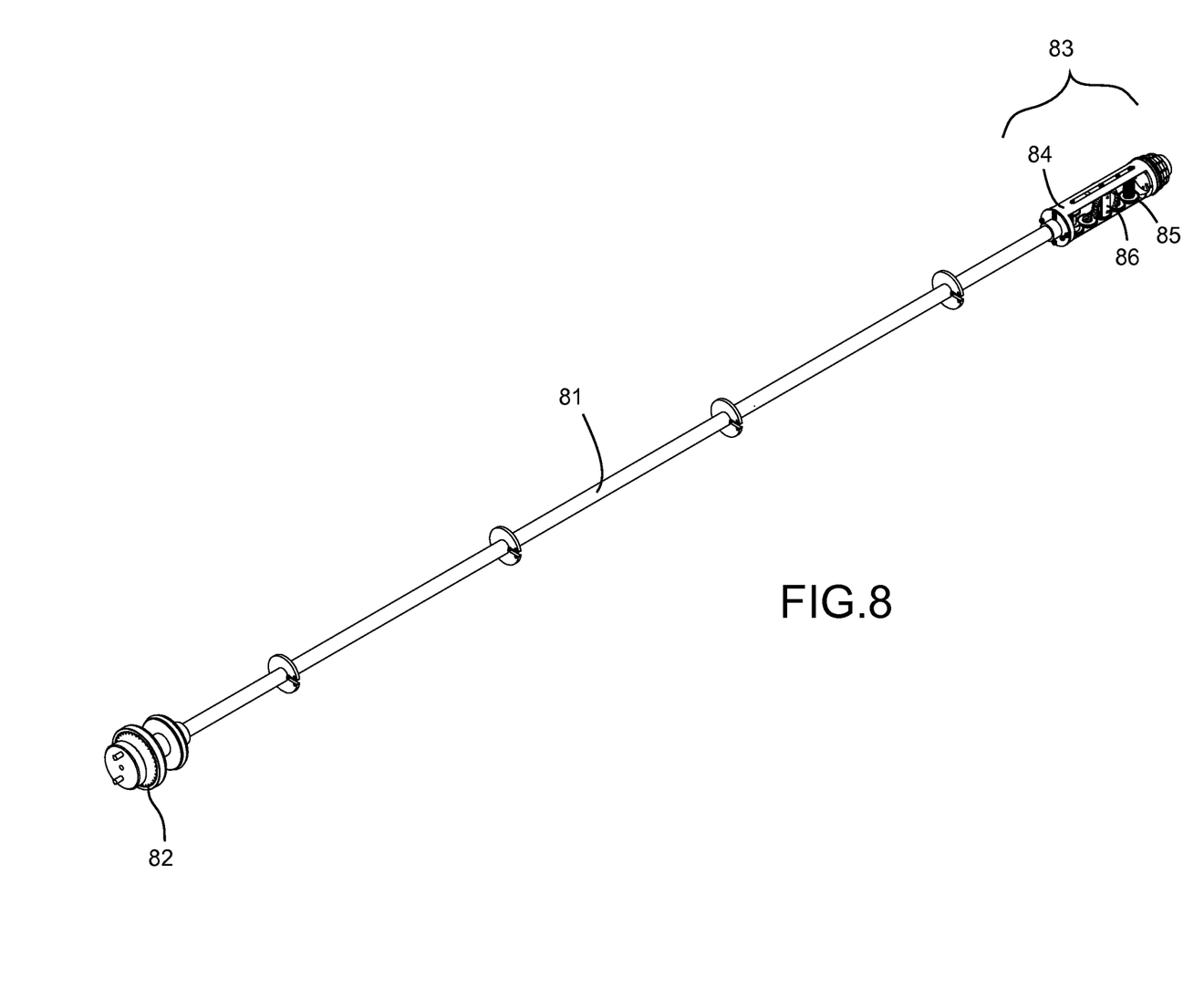
FIG. 8 shows a rotator probe configured to rotate an attached dilatometer cell for introducing various magnetic field characteristics during a testing procedure.

FIG. 8 shows a specimen probe configured to rotate an attached dilatometer cell at various angles for introducing various magnetic field characteristics during a testing procedure. The specimen probe is capable of rotational adjustment while the probe is inserted into the cryostat. This capability provides adjustable positioning of the dilatometer in between and during sample measurements. The rotator probe comprises an actuator 81 disposed at a proximal end of an actuating shaft 82, the actuating shaft extends from the proximal end to a distal end to a platform housing 83. The platform housing 83 contains a platform mount 86, the platform being coupled to the actuator shaft 82 via a geared mechanism 85 at a pivot 84. Thus, when the actuator 81 is adjusted by a user, at least a portion of the actuating shaft rotates, communicating movement through the pivot 84 and coupled geared mechanism 85, such that the platform 86 rotates accordingly, thereby rotating the dilatometer cell mounted thereon. In this regard, the dilatometer cell can be rotated within the cryostat at various angles (ex: 0 degrees, 90 degrees, etc.) with respect to an applied magnetic field.

This set up enables a user to study the physics of magnetostriction, which is the change in shape due to an applied magnetic field (usually found in ferromagnetic material). This change is caused by the magnetic field's interaction with a material's magnetic moment.

Alternatively, a static probe as illustrated in the embodiment of FIG. 5 may be used, however, in such embodiment the dilatometer must be removed from the probe and re-mounted thereon at a rotated orientation in order to accomplish measurements at various angles.

The invention claimed is:

1. An ultrasensitive ratiometric capacitance dilatometer cell, the dilatometer cell comprising:
   a first cell portion including at least one pair of planar surfaces;
   a second cell portion including at least one pair of planar surfaces;
   wherein the first cell portion is configured to nest with the second cell portion, the at least one pair of planar surfaces of the first cell portion and the at least one pair of planar surfaces of the second cell portion being separated by a gap defined therebetween to create at least first and second parallel plate capacitors based on respective opposing planar surfaces; and
   a channel extending across the gap from the first cell portion to the second cell portion, the channel including:
   a first wall at least partially defined by the first cell portion; and
   a second wall at least partially defined by the second cell portion, the second wall configured to oppose the first wall;
   wherein the first and second opposing walls are configured to receive a sample therebetween, the first and second walls being moveable relative to one another in a direction along a centerline of the dilatometer cell;
   wherein a shift of the at least one pair of planar surfaces of the first cell portion relative to the at least one pair of planar surfaces of the second cell portion reduces the capacitance of one of the first parallel plate capacitor or the second parallel plate capacitor, and increases the capacitance of the other one of the first parallel plate capacitor or the second parallel plate capacitor, as the sample varies in size between the first and second walls.

2. The dilatometer cell of claim 1, wherein the first and second cell portions are each composed of a dielectric material.

3. The dilatometer cell of claim 2, wherein said dielectric material is quartz.

4. The dilatometer cell of claim 1, wherein the first and second cell portions are each composed of a copper alloy.

5. The dilatometer cell of claim 1, comprising a Wheatstone bridge, wherein the first parallel plate capacitor forms a first leg and the second parallel plate capacitor forms a second leg of the Wheatstone bridge.

6. The dilatometer cell of claim 5, wherein a first inductor is coupled to the first parallel plate capacitor via a first conductive trace, and a second inductor is coupled to the second parallel plate capacitor via a second conductive trace to form four legs of the Wheatstone bridge.

7. The dilatometer cell of claim 6, wherein the first and second inductors are disposed outside of the dilatometer cell and connected via the conductive traces.

8. The dilatometer cell of claim 6, wherein at least one of the first and second inductors is disposed on or within the dilatometer cell.

9. The dilatometer cell of claim 1, wherein the first and second walls are configured to receive a sample having a characteristic length of about 2 mm.

10. The dilatometer of claim 1, further comprising a modular carrier interface for use with multiple mounting platforms, said platforms including a stationary platform and a rotator.

11. The dilatometer cell of claim 1, wherein the first and second parallel plate capacitors each include:
   a first pair of conductive plates associated with respective ones of the at least one pair of planar surfaces of the first cell portion; and
   a second pair of conductive plates associated with respective ones of the at least one pair of planar surfaces of the second cell portion;
   wherein the conductive plates of the first pair are configured to at least partially overlap with respective ones of conductive plates of the second pair.

12. The dilatometer cell of claim 11, wherein the first and second pairs of conductive plates comprise metallized surfaces of the first and second cell portions.

13. The dilatometer cell of claim 12, wherein said metallized surfaces comprise one or more of: platinum, gold, silver, or copper.

14. The dilatometer cell of claim 11, wherein each conductive plate of the first and second pairs of conductive plates spans a pre-determined area.

15. The dilatometer cell of claim 1, wherein each planar surface of the at least one pair of planar surfaces of the first cell portion is configured to oppose and overlap a different one of the planar surfaces of the at least one pair of planar surfaces of the second cell portion.

16. The dilatometer cell of claim 1, wherein the at least one pair of planar surfaces of the first cell portion are oriented at a first prescribed angle with respect to one another, and wherein the at least one pair of planar surfaces of the second cell portion are oriented at a second prescribed angle with respect to one another.

17. The dilatometer cell of claim 16, wherein the first cell portion includes at least one angled protrusion defined by the at least one pair of planar surfaces oriented at the first prescribed angle with respect to one another, and wherein the second cell portion includes at least one angled groove defined by the at least one pair of planar surfaces oriented at the second prescribed angle with respect to one another.

18. A dilatometer cell for providing a capacitance measurement for determining dimensional changes of a sample, the dilatometer cell comprising:
   a first cell portion including at least one angled protrusion defining first and second planar surfaces oriented at a prescribed angle with respect to one another;
   a second cell portion including at least one angled groove defining third and fourth planar surfaces oriented at the prescribed angle with respect to one another;
   wherein the first cell portion is configured to nest with the second cell portion such that the at least one angled protrusion of the first cell portion and the at least one angled groove of the second cell portion are separated by a gap defined therebetween to create at least first and second parallel plate capacitors which are oriented at the prescribed angle with respect to one another; and
   a channel extending across the gap from the first cell portion to the second cell portion, the channel including:
   a first wall at least partially defined by the first cell portion; and
   a second wall at least partially defined by the second cell portion, the second wall configured to oppose the first wall,
   wherein the first wall and the second wall are configured to receive the sample therebetween, the first and second walls being moveable relative to one another in a direction along a centerline of the dilatometer cell;
   wherein a shift of the first and second planar surfaces relative to the third and fourth planar surfaces reduces the capacitance of one of the first parallel plate capacitor or the second parallel plate capacitor, and increases the capacitance of the other one of the first parallel plate capacitor or the second parallel plate capacitor, as the sample varies in size between the first and second walls.

19. The dilatometer cell of claim 18, further comprising:
a third parallel plate capacitor; and
a fourth parallel plate capacitor,
   wherein the third and fourth parallel plate capacitors are disposed between the first and second cell portions.

20. The dilatometer cell of claim 18, wherein the first and second parallel plate capacitors each include:
   a first pair of conductive plates associated with respective ones the first and second planar surfaces; and
   a second pair of conductive plates associated with respective ones of the third and fourth planar surface,
   wherein the conductive plates of the first pair are configured to at least partially overlap with respective ones of conductive plates of the second pair.

21. The dilatometer cell of claim 18, wherein the prescribed angle comprises an acute angle.

22. The dilatometer cell of claim 18, wherein the prescribed angle comprises an obtuse angle.

* * * * *